(12) United States Patent
Fritzsch et al.

(10) Patent No.: US 11,639,717 B2
(45) Date of Patent: May 2, 2023

(54) PERESTALTIC PUMP AND DEVICE FOR ISOLATING CELLS FROM BIOLOGICAL TISSUE

(71) Applicant: Miltenyi Biotec B.V. & Co. KG, Bergisch Gladbach (DE)

(72) Inventors: Frederik Fritzsch, Cologne (DE); Ralf-Peter Peters, Bergisch Gladbach (DE)

(73) Assignee: Miltenyi Biotec B.V. & Co. KG, Bergisch Gladbach (DE)

( * ) Notice: Subject to any disclaimer, the term of this patent is extended or adjusted under 35 U.S.C. 154(b) by 293 days.

(21) Appl. No.: 16/833,694

(22) Filed: Mar. 30, 2020

(65) Prior Publication Data

US 2020/0324031 A1 Oct. 15, 2020

(30) Foreign Application Priority Data

Apr. 9, 2019 (EP) .................................. 19168101

(51) Int. Cl.
*F04B 43/14* (2006.01)
*A01N 1/02* (2006.01)
*A61M 60/279* (2021.01)

(52) U.S. Cl.
CPC ............ *F04B 43/14* (2013.01); *A01N 1/0247* (2013.01); *A61M 60/279* (2021.01)

(58) Field of Classification Search
CPC .... F04B 43/0063; F04B 43/02; F04B 43/028; F04B 45/04; F04B 45/10; C12M 21/08; C12M 29/10; C12M 29/12; A01N 1/0247
See application file for complete search history.

(56) References Cited

U.S. PATENT DOCUMENTS

| | | | | |
|---|---|---|---|---|
| 612,834 A | * | 10/1898 | Dieckmann | F04B 43/1269 417/477.12 |
| 3,152,553 A | * | 10/1964 | Rydberg | F04B 43/14 417/477.1 |
| 5,285,657 A | * | 2/1994 | Bacchi | A01N 1/0273 435/284.1 |
| 6,296,460 B1 | * | 10/2001 | Smith | F04B 43/14 417/475 |
| 6,962,488 B2 | * | 11/2005 | Davis | A61M 1/0058 604/153 |
| 8,747,084 B2 | * | 6/2014 | Richardson | F04B 43/1238 417/477.6 |
| 8,784,079 B2 | * | 7/2014 | Becker | F04C 9/005 417/477.2 |
| 2012/0207635 A1 | * | 8/2012 | Becker | F01C 9/005 418/49 |
| 2021/0059268 A1 | * | 3/2021 | Oda | A22B 5/04 |

* cited by examiner

*Primary Examiner* — Nathan C Zollinger
(74) *Attorney, Agent, or Firm* — Jaquelin K. Spong

(57) ABSTRACT

The invention is directed to a peristaltic pump (10), comprising: a flexible membrane (1) forming a at least one bladder (2) against a support, wherein each bladder is provided with one input orifice (4) which admits a fluid to the bladder (2) and one outlet orifice (5) which releases the fluid from the bladder (2); and at least one roller bearing (6) is configured to rotate about an axis (7) and to apply a compressive force against the at least one bladder (2). The peristaltic pump may be in fluid communication with a tapered jet (11).

12 Claims, 4 Drawing Sheets

PERESTALTIC PUMP AND DEVICE FOR ISOLATING CELLS FROM BIOLOGICAL TISSUE

CROSS REFERENCE TO RELATED APPLICATIONS

This US nonprovisional Patent Application claims priority to EP 19168101 filed Apr. 9, 2019. This prior application is incorporated by reference in its entirety.

STATEMENT REGARDING FEDERALLY SPONSORED RESEARCH

Not applicable.

STATEMENT REGARDING MICROFICHE APPENDIX

Not applicable.

BACKGROUND

The present invention is directed to a peristaltic pump and a device for isolating living target cells from biological tissue.

Cells which are strongly interconnected to form a biological tissue like epithelial cells are difficult to isolate into single, living cells from the tissue. While it is possible to mechanically destroy the infrastructure of the biological tissue and isolate single cells from the resulting debris, the thus obtained yield of living, unharmed cells is rather low.

It is known to isolate cells from organs in a more gentle perfusion process, but this requires cumbersome perfusion of the organ through an appropriate blood vessel with a sequence of buffer solutions. Such processes are known for the isolation of cardiomyocytes, or hepatocytes etc.

For example, US20110295149 discloses a device to solubilize tissue by an abrasive extraction of tissue fragments. The device is fixed on the tissue by vacuum and the cells are cut from the tissue with an abrasive component and further liquefied by appropriate enzymes.

EP3171152 discloses a device for isolating living target cells from biological tissue. This perfusion device comprises a two-part casing, a holder for a plurality of hollow penetration structures, and a support for the biological tissue which is positioned in the casing at a distance to the holder that the hollow penetration structures are forced into the tissue. Then, a release agent is administered through the hollow penetration structures into the tissue. Crucial to the device and method described in EP3171152 is to administer a fluid into a tissue with an appropriate rate of volume and pressure. EP3171152 mentions to this end a gear pump integrated in the casing or provided externally and connected to the device with an appropriate tubing set, but is silent on the type and technology of the pump. Further, the device according to EP3171152 is a disposable. As a pump integrated in the casing would be disposed with the device, the pump must be cheap to produce, small, and yet powerful enough to force fluids into a solid tissue.

Further, US 2019064144 discloses a peristaltic pump formed by tubes embedded in a flexible membrane against roller bearings are pressed. Due to the pressure of the roller bearings, the cross-section of the tubes is reduced, thereby increasing fluidic resistance. A substantial amount of the pressure applied will be distributed in the flexible membrane and will assist to the mechanical deformation of the tubes. Accordingly, this system will require a high mechanical load to provide a fluidic pressure and will have a tendency to create heat due to the mechanical deformation of the flexible membrane.

SUMMARY

Object of the invention is therefore a peristaltic pump (10), comprising a flexible membrane (1) forming at least one bladder (2) against a support (3), wherein each bladder is provided with one input orifice (4) which admits a fluid to the bladder (2) and one outlet orifice (5) which releases the fluid from the bladder (2); and at least one roller bearing (6) is configured to rotate about an axis (7) and to apply a compressive force against the flexible membrane.

Another object of the invention is a perfusion device for biological tissue comprising a support (12) and a clamp (13) to fix the biological tissue within a chamber (10), at least one tapered jet (11) configured to penetrate into the biological tissue and a lid (15) for the chamber wherein device further comprises a peristaltic pump which is in fluid communication with the tapered jet (11), wherein the peristaltic pump (10) comprises a flexible membrane (1) forming at least one bladder (2) against a support (3), wherein each bladder is provided with one input orifice (4) which admits a fluid to the bladder (2) and one outlet orifice (5) which releases the fluid from the bladder (2); and at least one roller bearing (6) is configured to rotate about an axis (7) and to apply a compressive force against the flexible membrane.

The preferable 2 or 4 roller bearings (6) are configured to apply a compressive force against the apex of the flexible membrane provided by the bladders (2) and the support. The compressive force reduces the volume of the bladder and/or increases the fluidic resistance within the bladder at the position of the roller bearing. By rotating the roller bearings, a fluid is pressed or pumped from the input orifice of the bladder to its output orifice (the input orifice being located upstream to the output orifice in direction of the rotation of the roller bearings).

PERISTALTIC PUMP OF THE INVENTION

Figure 1:
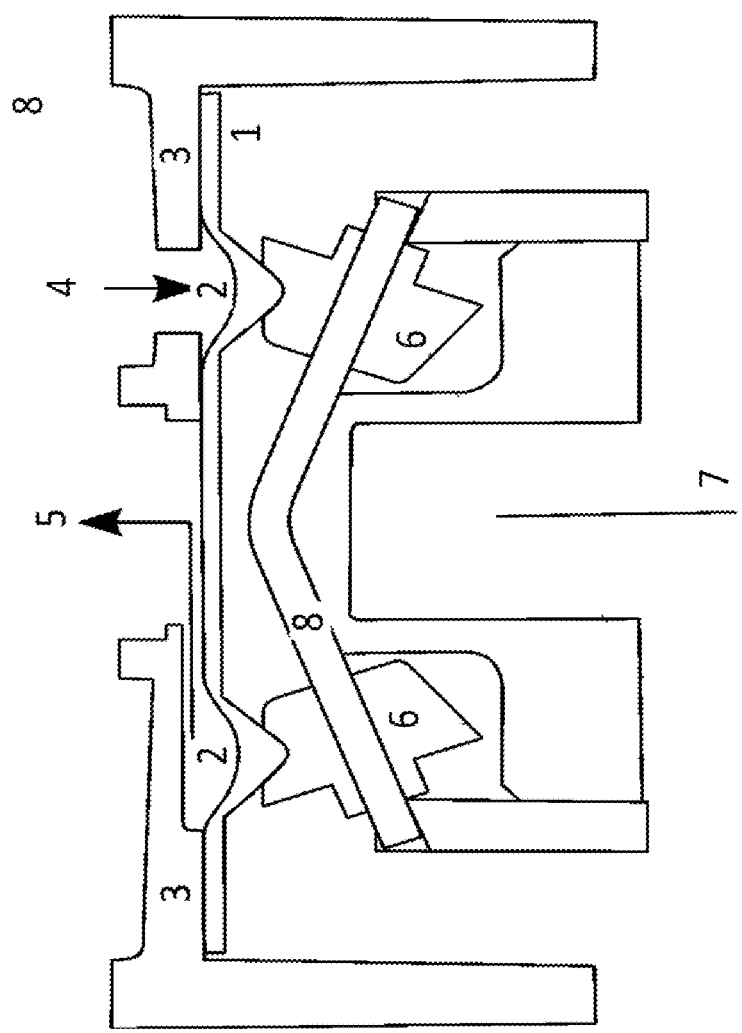
FIG. 1 shows a side view of the peristaltic pump

As shown in FIG. 1, the peristaltic pump of the invention comprises a flexible membrane (1) placed against a support (3). The flexible membrane (1) is provided with at least one channel, which forms with the support (3) one or more bladders (2). The channel or bladder is at one surface closed by the support, and at the other surface side formed as an apex (2' in FIG. 2). The bladder is therefore not embedded in the flexible membrane and/or formed as closed tube surrounded by the flexible membrane, but formed by the flexible membrane as an channel open the side of the support and extending from the surface of the flexible membrane in form of a bladder. In a preferred variant, the bladder has a thickness at the apex (2' in FIG. 2, i.e. the top of the bladder where the roller bearings (6) are in contact with the bladder) greater hat the thickness of the flexible membrane.

Against this apex, the least one roller bearing (6) is pressed in order to apply a compressive force against the flexible membrane, thereby reducing the volume of the bladder and/or increasing the fluidic resistance within the bladder at the position of the roller bearing. The at least one, preferable 2 or 4 roller bearings (6) are configured to rotate about an axis (7) by means of an appropriate motor (not shown). The flexible membrane (i.e. the bladder) is provided at locations within the channels with one input orifice (4) which admits a fluid to the bladder (2) and one outlet orifice (5) which releases the fluid from the bladder (2) during rotation of the roller bearings.

The flexible membrane (1) may be manufactured from any flexible and durable material like neoprene, silicone or rubber.

Preferable, the roller bearing (6) is provided with a with a pre-loaded spring to apply a compressive force against the at least one bladder (2). The tilted axis as shown in FIG. 1 has (inter alia) the same function as a pre-loaded spring.

The at least one bladder is preferable located at least in part in the path of the roller bearing (6) rotating about an axis (7). Preferable, one or more one bladders (2) are entirely positioned in the pathway of the rotating roller bearing (6), i.e. are at least in part circular shaped with a diameter of approximately the diameter of the pathway of the rotating roller bearing (6). For example. the bladder (2) may have a circular shape with a radius of 0.5 to 5 cm about the axis (7).

In another embodiment, one or more one bladders (2) are only in part (like for 50% of the length) positioned in the pathway of the rotating roller bearing (6). In this variant, the channels/bladders may be linear shaped, but need to be oriented around the axis of the roller bearing.

If a plurality of bladders is provided, the bladders may be provided with a fluidic pathway between the outlet orifice (5) of a first bladder and the input orifice (4) of a second bladder. The inlet orifice of the first bladder is then identical to the one input orifice (4) which admits a fluid to the bladders (2) and the output orifice of the last bladder (in direction of flow/rotation of the bearings) is identical to the one outlet orifice (5) which releases the fluid from the bladders.

In another variant of providing a plurality of bladders, the bladders are provided with a common fluidic pathway from the outlet orifices (5) of the bladders and a common tubes to the input orifices (4) of the bladders.

The bladders (2) may have total fluid volume of about 1 to 10 microliters when filled with fluid.

Figure 2:
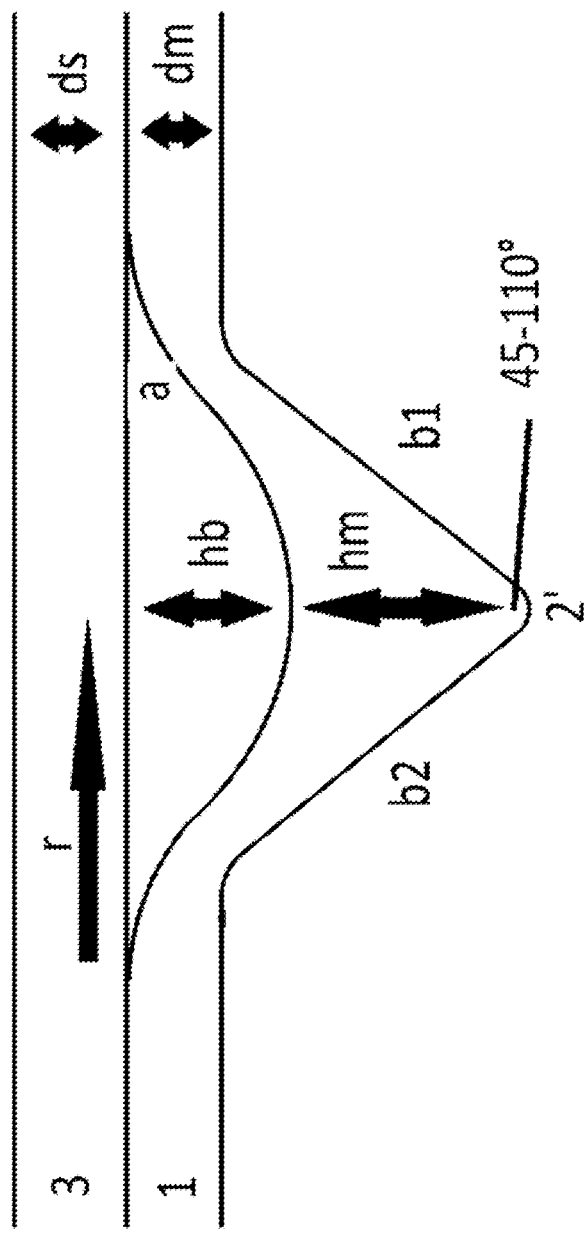
FIG. 2 shows the bladder area of the flexible membrane located against the support

As shown in FIG. 2, the maximum height of the bladder (hb) is 0.5 to 2 mm, preferable 0.8 to 1.2 mm. The thickness (hm) of the flexible membrane at the location where the roller bearing presses against the bladder (2' in FIG. 2) is 0.5 to 2 mm, preferable 1.0 to 1.5 mm, wherein the thickness (dm) of the membrane itself is about 0.3 to 0.7 mm.

Depending on the desired flow of volume and/or pressure, the roller bearing (6) rotates about the axis (7) at a speed of 10 to 5000 revolutions/minute.

Preferable, the least one roller bearing (6) is configured to rotate about an axis (7) perpendicular to the at least one bladder (2) and/or the support. By way of this combination of compressive force against the flexible membrane and rotation about axis (7), fluids are pressed through the bladder from the first input orifice and to the last output orifice.

In other words, the compressive force applied by least one roller bearing (6) against the bladder (2) increases the flow impedance of the bladder at the position of the roller bearing (6) by 10 to 100-fold.

In order to increase the flowrate of the fluid through the bladder without applying too high compressing force resulting in creation of undesired heat, the bladder (2) may have a shape with an apex angle (shown as 2' in FIG. 2 as angle between b1 and b2) against which the roller bearing (6) presses, wherein the apex angle is between 45 and 110, preferable 70 to 100 degrees.

The shape of the bladder may further be described by the angle shared by the bladder and the support as shown with (a) in FIG. 2. This angle is preferable between 10 and 90 degrees, especially between 20 and 60 degrees.

The bladder (2) is preferable lens-shaped and may have an internal lumen with an aspect ratio of height to width of 0.1 to 1.0 (in FIG. 2: 2 r/hb). If more than one bladder is provided, the bladders have an identical shape and/or internal lumen.

As shown in FIG. 1, the roller bearings have preferable a non-cylindrical form, but are formed as a cone. This shape avoided the build-up of heat in the device due to shear forces induced in the flexible membrane by the rotating roller bears. In this embodiment, the axis (8) of the roller bearings (6) is provided with the same form or angle as the roller bearings (6) i.e. axis (8) is tilted and not orthogonal to rotational axis (7).

Perfusion Device of the Invention

Due to its compact design and high fluidic pressure, the peristaltic pump as described may be used advantageously as a part of a perfusion device for biological tissue. As already discussed, such perfusion devices are used to administer a fluid (a release agent) like an enzyme into a biological tissue with an appropriate rate of volume and pressure in order to disintegrate the tissue at least in part and/or to release cells from the biological tissue. To this end, hollow penetration structures like hollow needles are forced into the tissue and the release agent is pumped through the hollow penetration structures into the tissue. In order to provide a satisfactory release rate of cells, the release agent needs to be pumped at a sufficient flow rate or pressure through the tissue.

The term "disaggregation of a biological tissue into target cells" refers to any process where cell structures, cell aggregates or cell matrices are at least in part destroyed without killing, destroying or lysing the target cells. At best, the target cells are obtained as single, isolated and living cells. For example, if liver is used as biological tissue, an appropriate enzyme is administered into the liver with the device of the invention. The liver tissue is disaggregated to yield single liver cells which do not leave the liver. To harvest the target cells, the epithelial cell sheet of the liver (the capsule of the liver) is mechanically opened and the liver cells can be washed from the remaining tissue.

Figure 3:
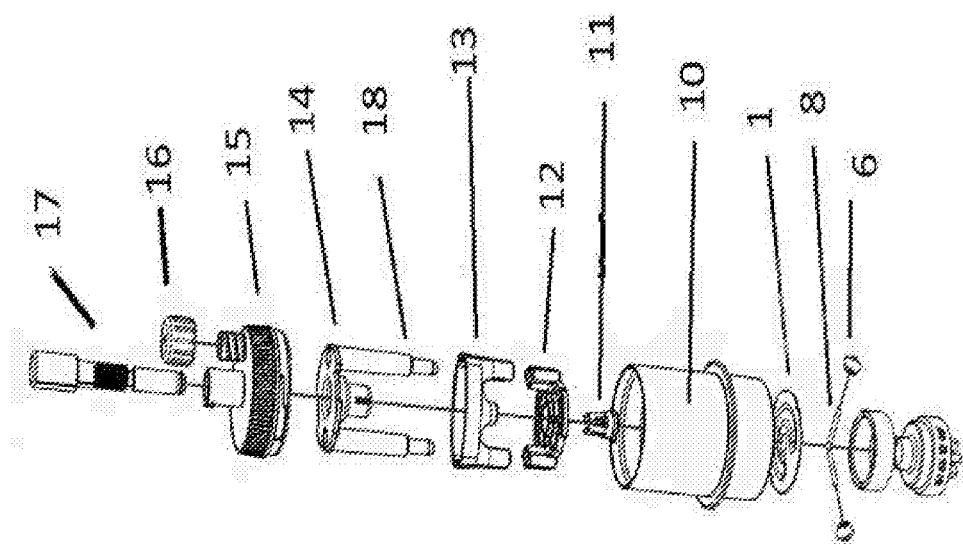
FIG. 3 shows the components of the perfusion device

FIG. 3 shows by way of example the perfusion device of the invention with several variants. Common for all embodiments of the device is the peristaltic pump as already disclosed being in fluid communication to at least one tapered jet (11) which is configured to penetrate into the tissue. By penetrating into the tissue, a fluid is administered into the tissue. The device comprises a cylindrical shaped chamber (10) which may bye closed at one end with lid (15) and the other end with the peristaltic pump (depicted as 1,8,6). The tissue is introduced into the chamber on support (12) and mechanically fixed by a clamp (13) in order to be penetrated by the tapered jet (11).

The device of the invention may in a first embodiment comprise a lid (15) with a downholder (14) configured to be attached to the clamp (13).

Further, the lid (15) may comprise a adjuster (17), configured to be attached to the downholder (14) and/or the lid (16) may comprise at least one orifice (16), optionally having a Luer lock.

In another embodiment, the downholder (14) comprises at least one tube (18) extending from the lid into the chamber (10) to the support (12).

The perfusion device according to the invention has the advantage that only the parts having mechanical contact to the biological tissue, i.e. the holder for the plurality of the tapered jet (11) the support, are single-use disposables, whereas the components of the device like the chamber the lid can, after appropriate cleaning, be used multiple times. In a variant, of the invention, the whole device including all components is provided as disposable.

The agent to disaggregate the biological tissue (6) and/or the buffer is pumped by the peristaltic pump into the biological tissue (6) as long as needed to extracted the desired cells from the tissue.

Preferable, the tapered jet (11) is provided with means to stop the flow of reagents through a needle when the opening of a needle is placed not within the biological tissue, i.e. in case a needle did not penetrate into the tissue or penetrated through the tissue.

The tapered jet (11) may have an outer diameter at the basis of 0.05 to 5 mm, preferably 0.2 to 1 mm, most preferably 0.3 to 0.7 mm and independently, an inner diameter at the basis of 0.02 to 4 mm, preferably 0.1 to 1 mm, most preferably 0.1 to 0.6 mm and independently a length of 1 to 100 mm, preferably 2 to 20 mm, most preferably 4 to 5 mm.

The number of the tapered jets (11) depends on the size of the biological tissue and may vary between 2 and 50, preferably between 5 and 25. The tapered jets (11) may be arranged in any geometry or array on the holder and may have the same or different length. The holder may be not mechanically fixed in main casing. This enables the use of different chambers with different number of tapered jets (11) and/or different length of tapered jets (11) and/or different geometry or array of tapered jets (11), depending on the size and thickness of the biological tissue.

Depending on the size, thickness and the outer form of the biological tissue, the penetration depth of the tapered jets (7) may be adjusted by adjustor (17), which presses against downholder (14) and clamp (13) and finally against the biological tissue.

The disclosed components of the device of the invention may be produced from the same or different material like stainless steel, polyacrylamide, polystyrene, polyolefins like polyethylene and polypropylene, polycarbonate, polyoxymethylene, polymethylmethacrylate, poly lactic acid or polyamides.

The device of the invention may be manufactured by any method known to a person skilled in the art. Preferred methods are injection molding and 3D printing, for example by extrusion deposition, fused deposition modeling, stereolithography or photopolymer digital light processing The term "penetration" as used herein means that the needles are placed into the biological tissue in order to administer the release agent into the biological tissue. It is not desired to pierce or puncture the needles through the biological tissue since the release agent would then not or not sufficiently enter the biological tissue to release the target cells. It should be taken care in the process of the invention that the majority of the needles are placed inside the biological tissue and do not pierce or puncture through the biological tissue. At best, all needles are placed into the biological tissue at 30-70%, preferable approximately 50% of its thickness.

Biological Tissue

The device of the invention can be used for all types of biological tissue, like organs of vertebrates or invertebrates, preferably to spleen, heart, liver, brain and other neural tissues, kidney, lung, pancreas, breast, umbilical cord, skin, placenta, ovary, oviduct, uterus, prostate, tonsil, thymus, stomach, testis, trachea, cartilage, tendon, bone, skeletal muscle, smooth muscle, gut, colon, intestine, bladder, urethra, eye, gall bladder, organoids from cell cultures and tumors.

Target Cells

The device of the invention can be used to generate all type of target cells which are tissue-resident cells, especially cells from vertebrate or invertebrate tissue, preferably epithelial cells, endothelial cells, fibroblasts, myofibroblasts, hepatocytes, hepatic stellate cells, cardiomyocytes, podocytes, keratinocytes, melanocytes, neuronal cells including neurons, astrocytes, microglia and oligodendrocytes, leukocytes including dendritic cells, neutrophils, macrophages and lymphocytes, including T cells, B cells, NK cells, NKT cells and innate lymphoid type 1-3 cells, tissue stem cells including MSCs and progenitor cells of cells mentioned above.

Disaggregating Agents

The fluids administered into the tissue may comprise "disaggregating agents", the term relating to any fluid like a buffer comprising a substance used to destroy the anchorage of target cells within the tissue without influencing the target cells itself. This anchorage derives from interactions of the cells with the extracellular matrix or with adjacent cells. These interactions, e.g. tight junctions, gap junctions, desmosomes, and hemidesmosomes, are built mainly by proteins, e.g. cadherins, connexins, claudins and integrins, mostly in a calcium-dependent manner Therefore, the release agent which destroys the tissue integrity may contain a calcium-free and/or a calcium-depleting agent and/or enzymes that degrade the extracellular matrix or extracellular protein-protein interactions. The administration of the components of the release agent may be sequentially or simultaneously.

For example, the agent to disaggregate the biological tissue (6) is selected from the group consisting of trypsin, chymotrypsin, papain, collagenase, elastase, dispase, thermolysin, hyaluronidase, clostripain and neutral protease from clostridium histolyticum, pronase, DNase I, pepsin, proteinase K, lysozyme, chelating agents for bivalent ions (like EDTA or citrate) and mixtures thereof.

Preferred is a sequestered application of a calcium-free or calcium-depleting buffer followed by an enzyme-containing buffer which degrades the extracellular matrix or extracellular protein-protein interactions. The calcium-depleting reagent may be a buffer containing EDTA, EGTA or citrate.

Handling of the Device/Process of the Invention

Figure 4:
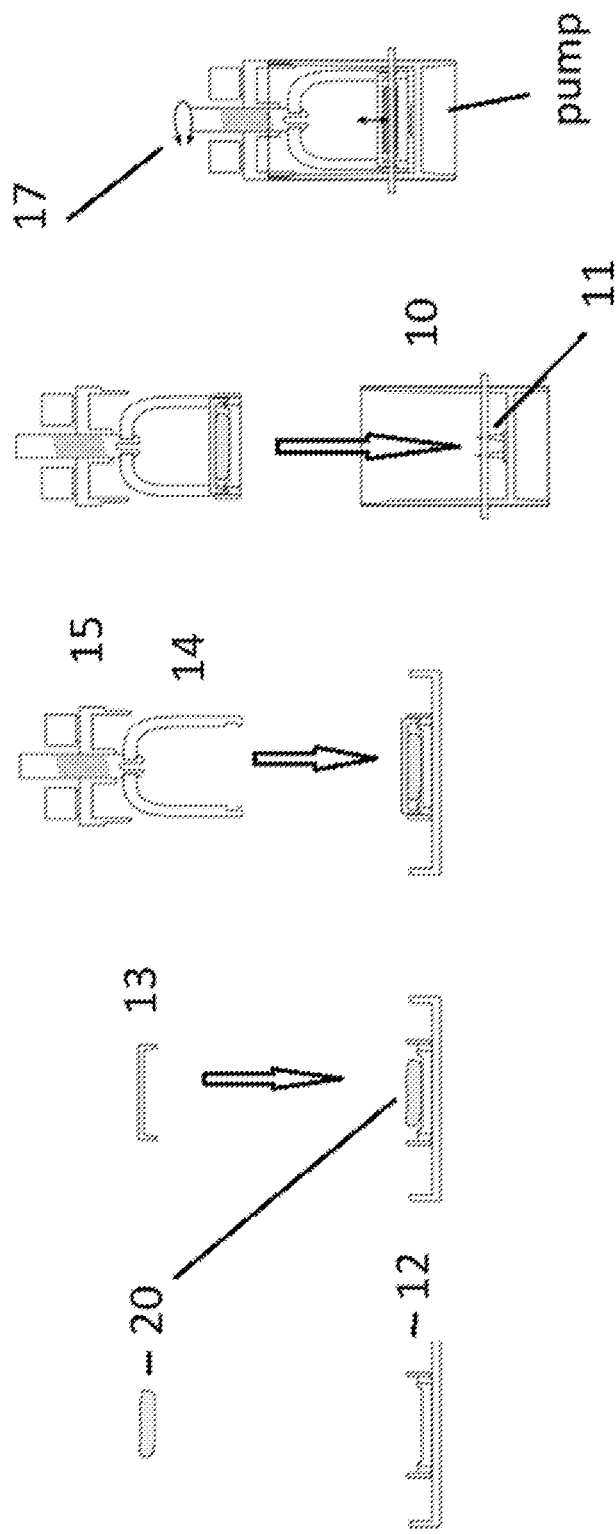
FIG. 4 shows how a sample of tissue is inserted into the perfusion device

FIG. 4 shows schematically the use of the device. First, support (12) is placed on a dish and tissue (20) is placed on the support (12). Then, tissue (20) is fixated on the support (12) by clamp (13). Support (12) and clamp (13) may be provided with means (like notches) to mechanically interlock with each other to prevent separating the components under operating conditions of the device. To this "stack", already combined lid (15) and downholder (14) is attached and the resulting construction is then inserted into chamber (10) comprising tapered jets (11). Preferable, lid (15) and chamber (10) are provided with threads to ensure a watertight connection. The penetration depth of the tapered jets (11) into the tissue (20) may be adjusted by adjustor (17), preferable provided with a thread for adjustment. In FIG. 4, the peristaltic pump as already disclosed is omitted, but may be attached to the chamber as shown by the term "pump".

What is claimed is:

1. A perfusion device for biological tissue comprising a support (12) and a clamp (13) to fix the biological tissue within a chamber (10), at least one tapered jet (11) configured to penetrate into the biological tissue and a lid (15) for the chamber characterized in that the device further comprises a peristaltic pump which is in fluid communication with the at least one tapered jet (11), wherein the peristaltic pump comprises:
   a flexible membrane (1) forming at least one bladder (2) against a support (3), wherein each bladder is provided with one input orifice (4) which admits a fluid to the bladder (2) and one outlet orifice (5) which releases the fluid from the at least one bladder (2); and at least one roller bearing (6) is configured to rotate about an axis (7) and to apply a compressive force against the at least one bladder (2), wherein the at least one bladder has a shape with a protruding apex angle against which the at least one roller bearing (6) presses, wherein the apex angle is between about 45 and about 110 degrees, and wherein the at least one bladder is formed as open channel against the support (3) and a protruding apex from the plane of the flexible membrane.

2. The peristaltic pump according to claim 1, characterized in that the at least one bladder is located at least in part in the path of the at least one roller bearing (6) rotating about the axis (7).

3. The peristaltic pump according to claim 1, wherein the at least one bladder comprises a plurality of bladders, characterized in that the plurality of bladders is provided with a fluidic pathway between the outlet orifice (5) of a first bladder and the input orifice (4) of a second bladder.

4. The peristaltic pump according to claim 1, wherein the at least one bladder comprises a plurality of bladders, and where each of the plurality of bladders has an input connected to a common fluidic pathway and each of the plurality of bladders also has an output connected to another common fluidic pathway.

5. The peristaltic pump according to claim 1, characterized in that the at least one bladder is configured such that the compressive force applied by the at least one roller bearing (6) against the at least one bladder (2) increases the flow impedance of the bladder at the position of the at least one roller bearing (6) by 10 to 100-fold.

6. The peristaltic pump according to claim 1, characterized in that the at least one bladder (2) has an internal lumen with an aspect ratio of height to width of 0,1 to 1,0.

7. The peristaltic pump according to claim 1, characterized in that the at least one roller bearing (6) is configured to rotate about the axis (7) perpendicular to the at least one bladder (2) and/or the support (3).

8. The peristaltic pump according to claim 1, characterized in that the at least one roller bearing is formed as a cone and an axis (8) of the at least one roller bearing (6) is provided with the same form or angle as the at least one roller bearing (6).

9. The perfusion device according to claim 1, characterized in that the lid (15) comprises a downholder (14) configured to be attached to the clamp (13).

10. The perfusion device according to claim 1, characterized in that the lid (15) comprises a adjuster (17), configured to be attached to the downholder (14).

11. The perfusion device according to claim 1, characterized in that the support (12) and the clamp (13) are configured to be mechanically combined and wherein a lower part (40) is configured to support the tissue and an upper part (50) is configured to press the tissue against the lower part (50).

12. The perfusion device according to claim 1, characterized in that the downholder (14) comprises at least one tube (18) extending from the lid into the chamber (10) to the support (12).

* * * * *